US00PP27284P3

(12) United States Plant Patent
Lehrer et al.

(10) Patent No.: US PP27,284 P3
(45) Date of Patent: Oct. 18, 2016

(54) ***VERONICA* PLANT NAMED 'BLUE YONDER'**

(50) Latin Name: *Veronica×hybrida*
Varietal Denomination: Blue Yonder

(71) Applicants: Karen A. Lehrer, Fort Collins, CO (US); Kirk C. Fieseler, Fort Collins, CO (US)

(72) Inventors: Karen A. Lehrer, Fort Collins, CO (US); Kirk C. Fieseler, Fort Collins, CO (US)

( * ) Notice: Subject to any disclaimer, the term of this patent is extended or adjusted under 35 U.S.C. 154(b) by 81 days.

(21) Appl. No.: 14/545,000

(22) Filed: Mar. 13, 2015

(65) Prior Publication Data

US 2016/0278266 P1 Sep. 22, 2016

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt

(74) *Attorney, Agent, or Firm* — Barbara Campbell; James M. Weatherly; Cochran Freund & Young, LLC

(57) ABSTRACT

A new cultivar of *Veronica* plant named 'Blue Yonder' that is characterized by a low spreading habit, violet-blue flowers, and dark green semi glossy foliage, is disclosed.

3 Drawing Sheets

Genus and species: *Veronica×hybrida.*
Variety denomination: 'Blue Yonder'.

BACKGROUND OF THE NEW PLANT

The present invention relates to a new and distinct cultivar of speedwell plant grown as an ornamental plant for use in border, rock garden, and as a groundcover for the landscape. The new variety is known botanically as *Veronica×hybrida* and will be referred to hereinafter by the cultivar name 'Blue Yonder'.

'Blue Yonder' is a hybrid plant of unknown species which in part botanically resembles plants of the species *Veronica allionii* and *Veronica liwanensis* (the latter commonly known as Turkish Speedwell). The inventor is not able to definitively attribute 'Blue Yonder' to either these two or any other species. Commencing in spring 2010, the inventor assembled many self-sown hybrid *Veronica* seedlings at the inventor's nursery in Fort Collins, Colo. The inventor discovered 'Blue Yonder' in the inventor's trial and display gardens at the inventor's nursery as a chance seedling amongst the self-sown seedlings.

The inventor was attracted to the rich intense blue flowers of 'Blue Yonder' which set it apart from all other seedlings on the nursery. In addition, plants of 'Blue Yonder' bear rich dark green foliage on creeping and self-rooting dark stems. The overall effect of 'Blue Yonder' in containers and in the landscape is of a dense mat of foliage covered in spring and early summer with many densely packed racemes consisting of numerous (up to 80) blue-violet single flowers. The flowers are the more conspicuous by virtue of a near-white corolla tube eye and dark stamens with near-white anthers.

'Blue Yonder' was first asexually propagated by the inventor in Fort Collins, Colo. in 2010 using the method of stem cuttings rooted in perlite under intermittent mist. The inventor has carried out multiple asexual reproductions and has established that 'Blue Yonder' is uniform and stable and reproduces true to type from its cuttings.

SUMMARY

The following traits have been repeatedly observed and represent the distinguishing characteristics of the new *Veronica* variety known as 'Blue Yonder.' 'Blue Yonder' has not been tested under all possible conditions and phenotypic differences may be observed with variations in environmental, climatic, and cultural conditions, however, without any variance in genotype. Growing requirements are similar to the species.

3. 'Blue Yonder' exhibits a low spreading habit.
4. 'Blue Yonder' exhibits rich dark green semi-glossy foliage.
5. 'Blue Yonder' exhibits violet-blue flowers borne in profusion on long racemes.
6. The flowers of 'Blue Yonder' bear a contrasting near-white eye which arises from the color of the corolla tube.
7. The stamens of 'Blue Yonder' are dark blue and prominently exserted, and bear near-white anthers which also contrast with the dark blue flowers.
8. 'Blue Yonder' reaches 10 cm in height and 40 cm in width at maturity.
9. 'Blue Yonder' blooms profusely from late spring through summer.
10. 'Blue Yonder' is hardy to USDA Zone 4.

DESCRIPTION OF THE PHOTOGRAPHS

The accompanying color photographs illustrate the overall appearance of the new *Veronica* variety named 'Blue Yonder' showing colors as true as it is reasonably possible to obtain in colored reproductions of this type. Color in the photographs may differ from color values cited in the detailed botanical description, which accurately describe the actual color of the new *Veronica* variety named 'Blue Yonder'. All drawings were made using conventional techniques and although foliage colors may appear different from actual colors due to light reflectance, they are as accurate as possible by conventional photography.

DESCRIPTION OF THE NEW VARIETY

Figure 1:
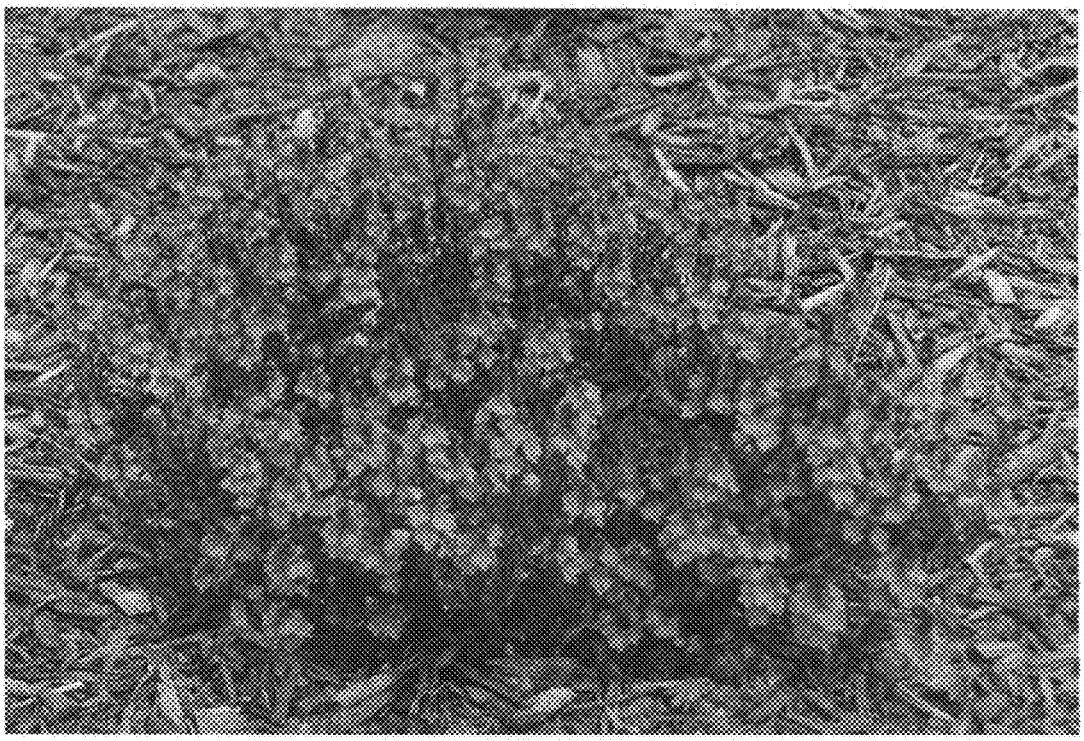
FIG. 1 depicts a one-year-old plant which has been established as an in-ground planting in a secure and private trial garden in Lancaster, Pa.
Figure 2:
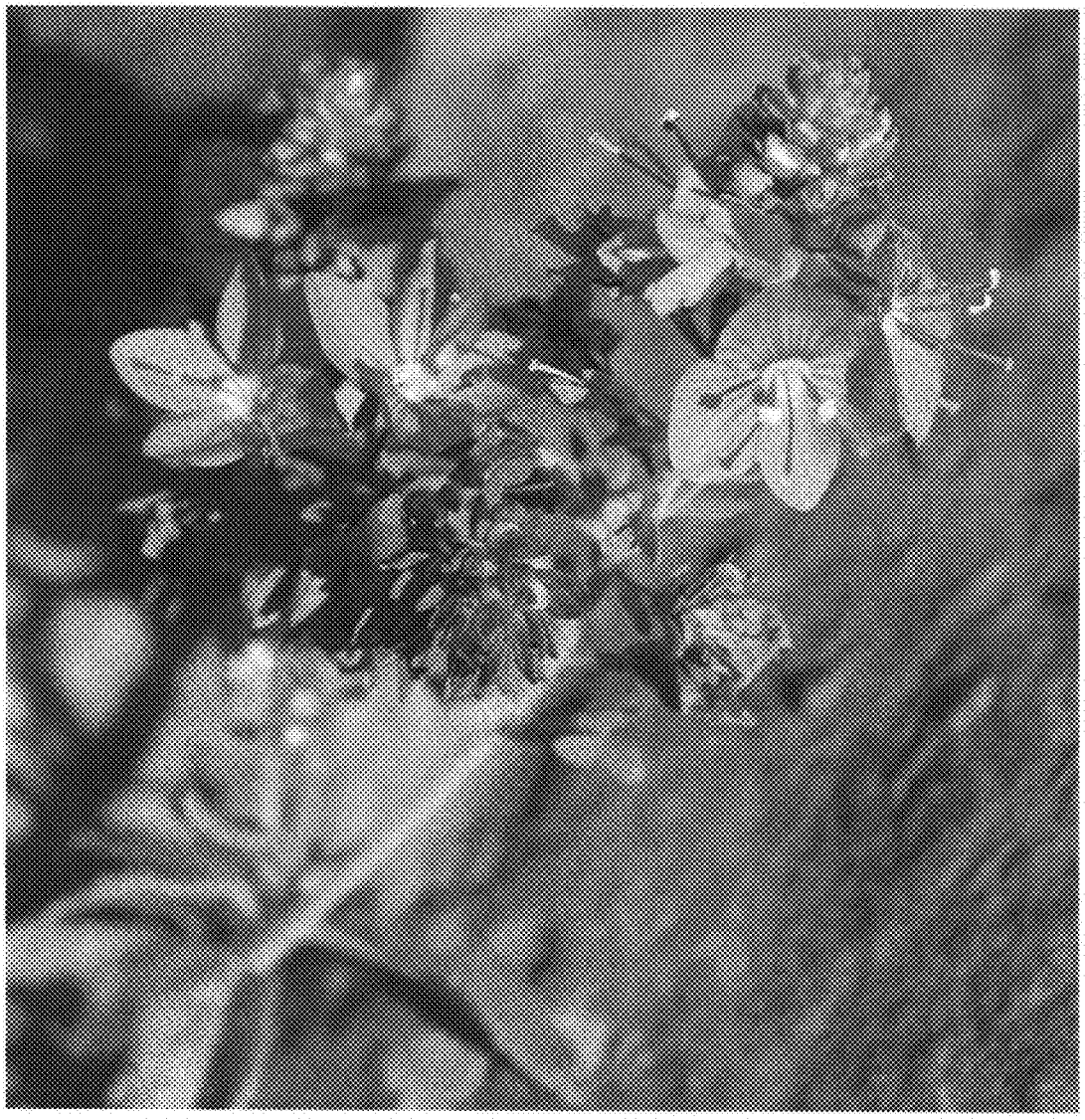
FIG. 2 is a close up of the inflorescence of 'Blue Yonder'.
Figure 3:
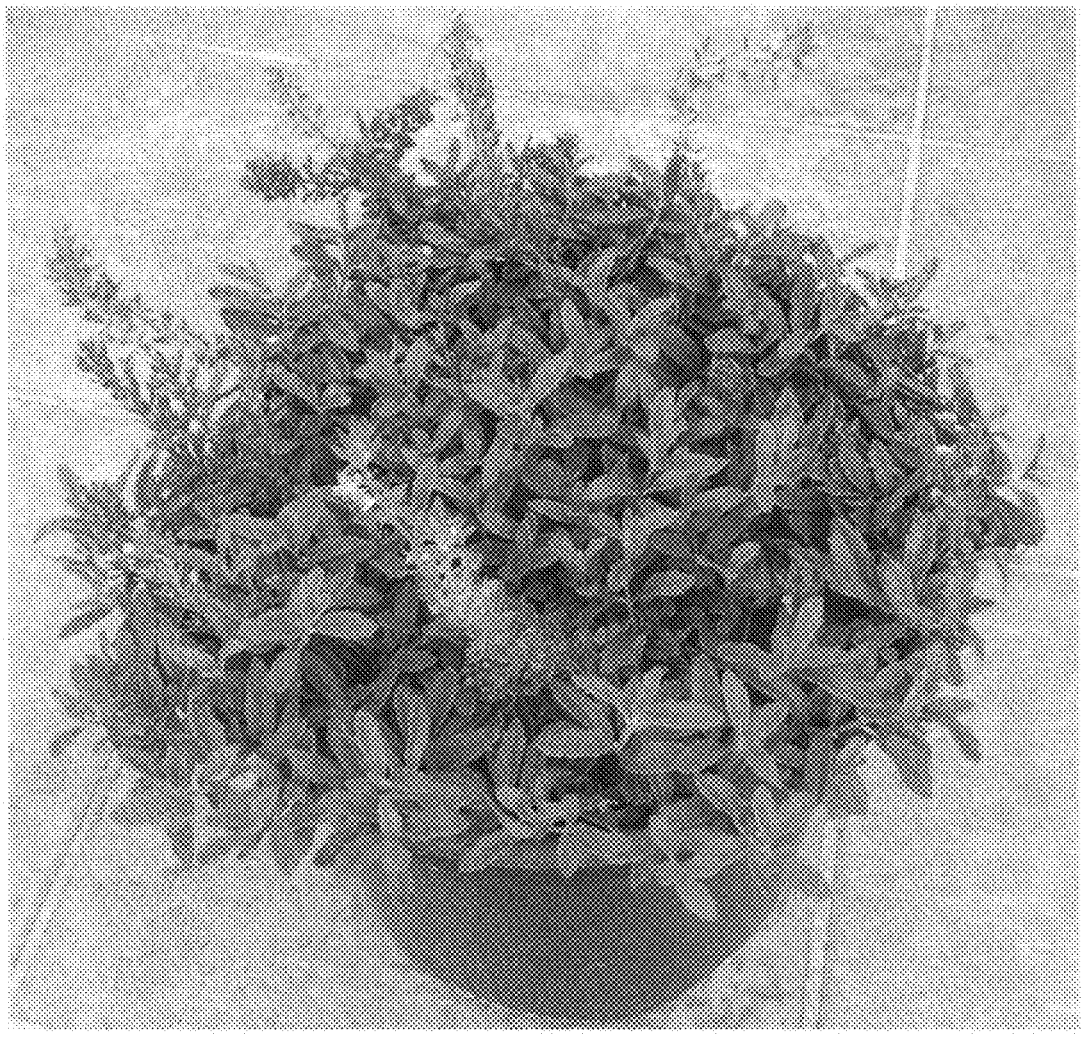
FIG. 3 depicts a 15-month-old plant which has grown and spread to fill a 2-gallon container outdoors in Santa Barbara, Calif. This photograph was made from a photograph taken in mid-July when flowering is almost finished.

The following is a detailed description of the new *Veronica* cultivar named 'Blue Yonder'. Data was collected in Santa Barbara, Calif. from an established 15 month old plant which was growing out of doors in a 2-gallon container. Phenotypic differences may be observed with variations in environmental, climatic, and cultural conditions, without however, any difference in genotype. Color determinations are in accordance with the fifth edition (2007) of The Royal Horticultural Society Colour Chart except where general color terms of ordinary dictionary significance are used. The growing requirements are similar to the species.

Botanical classification:

*Family.*—Scrophulariaceae.

*Genus and species.*—*Veronica*×*hybrida.*

*Denomination.*—'Blue Yonder'.

*Common name.*—Speedwell.

Parentage: Unknown parentage; 'Blue Yonder' is a chance seedling and a hybrid plant of unknown species which in part botanically resembles plants of the species *Veronica allionii* and *Veronica liwanensis* (the latter commonly known as Turkish Speedwell).

Plant:

*Plant type.*—Herbaceous perennial ground cover.

*Plant use.*—Border, rock garden, in containers and as a groundcover for the landscape.

*Plant vigor.*—Moderate.

*Branching habit.*—Basal branching.

*Dimensions at maturity.*—10 cm in height and 40 cm in width.

*Plant hardiness.*—USDA Zone 4.

*Asexual propagation method.*—Softwood cuttings and division.

*Growth habit.*—Low and spreading; stems may root where a node is in contact with soil surface; variety makes a good ground cover.

*Root system.*—Fibrous.

*Cultural requirements.*—Plant in well-draining soil, and full sun with adequate but not excess water.

*Time to initiate roots.*—2 weeks to develop roots on an initial cutting.

*Crop time.*—8 to 10 weeks from a rooted cutting to a finished commercial 1-liter container.

*Seasonal interest.*—Flowers from late spring and early summer.

Stem:

*Stem shape.*—Cylindrical.

*Stem surface.*—Puberulent.

*Stem length.*—10 cm to 15 cm.

*Stem diameter.*—15 mm.

*Stem color.*—178B.

*Internodal distance.*—Ranges from 0.5 cm to 2.0 cm.

Foliage:

*Leaf arrangement.*—Opposite.

*Leaf division.*—Simple.

*Leaf shape.*—Elliptic.

*Leaf apex.*—Rounded.

*Leaf base.*—Cuneate.

*Leaf attachment.*—Sessile.

*Leaf margin.*—Crenate.

*Leaf surface* (*adaxial surface*).—Glabrous.

*Leaf surface* (*abaxial surface*).—Matte, lightly scabrous.

*Leaf length.*—Ranges from 20 mm to 35 mm.

*Leaf width.*—Ranges from 7 mm to 11 mm.

*Leaf color* (*both surfaces*).—143A.

*Venation pattern.*—Pinnate.

*Vein color* (*both surfaces*).—143A.

*Foliar fragrance.*—None observed.

Inflorescence:

*Inflorescence type.*—Terminal raceme.

*Inflorescence dimensions.*—22 cm in length and 18 cm in width.

*Inflorescence quantity.*—Ranges from 25 to 30 per 1-liter container plant.

*Blooming season.*—Late spring through summer.

*Flower quantity.*—Approximately 80 per inflorescence.

*Flower shape.*—Funnelform.

*Flower dimensions.*—10 mm in diameter and 4 mm in depth.

*Distance between flowers.*—4 mm to 5 mm.

*Corolla tube depth.*—1 mm.

*Number of petals.*—4 in number.

*Petal color* (*adaxial and abaxial surfaces*).—94A fading (aging) to 94B.

*Corolla tube color.*—NN155B.

*Petal length.*—Ranges from 4 mm to 5 mm per individual flower.

*Petal width.*—Ranges from 3 mm to 4 mm per individual flower.

*Petal shape.*—Broadly obovate.

*Petal apex.*—Rounded.

*Petal base.*—Truncate.

*Petal margin.*—Entire.

*Petal surface* (*adaxial and abaxial surfaces*).—Glabrous.

*Peduncle length.*—Average is 4 mm.

*Peduncle diameter.*—0.5 mm.

*Peduncle color.*—137D.

*Peduncle shape.*—Cylindrical.

*Peduncle surface.*—Smooth.

*Calyx shape.*—Stellular.

*Calyx diameter* (*when flattened*).—8 mm.

*Calyx color.*—137D.

*Sepals* (*two pairs: one pair of adjacent long sepals which is opposite to one short pair of adjacent short sepals*).—In total, 4 in number.

*Sepals fused or unfused.*—Unfused.

*Sepal dimensions.*—Longer pair 7 mm in length×2 mm in width, shorter pair 3 mm to 4 mm in length×1 mm in width.

*Sepal shape.*—Lanceolate.

*Sepal margin.*—Entire.

*Sepal color* (*adaxial and abaxial surfaces*).—137D.

*Sepal apex.*—Acute.
*Sepal surface.*—Smooth.
*Bud dimensions.*—3 mm in length and 1.5 mm in diameter.
*Bud color.*—95B.
*Bud shape.*—Ovoid.
*Bud surface.*—Smooth.
*Bud apex.*—Acute.
*Flower fragrance.*—None observed.

Reproductive organs:
*Stamens.*—2 in number, 1 adnate to base of corolla tube.
*Stamen length.*—5 mm.
*Anther shape.*—Club, bifid.
*Stamen color.*—95B.
*Anther dimensions.*—1 mm in length and less than 0.50 mm in width.
*Anther color.*—95B.
*Pollen.*—Moderate amount, color NN155B.
*Pistil.*—1 in number.
*Pistil length.*—4 mm.
*Pistil color.*—103A.
*Stigma shape.*—Bi-lobed, rounded.
*Stigma surface.*—Glossy.
*Stigma color.*—85D.
*Stigma height.*—Less than 0.50 mm.
*Ovary shape.*—Globose.
*Ovary dimensions.*—Less than 1 mm in diameter and less than 1 mm in height.
*Ovary color.*—145D.
*Ovary position.*—Superior.

Seed: No seed observed to date.

COMPARISON TO PARENTAL LINES AND COMMERCIAL VARIETY

'Blue Yonder' cannot be compared with its unknown parents, but can be compared with two other prostrate *Veronica* varieties which are the closest known to the inventor: *Veronica* 'Reavis' (unpatented) which is a described as a hybrid of *Veronica liwanensis*, and *Veronica* 'Tidal Pool' (U.S. Plant Pat. No. 23,341).

In comparison with 'Blue Yonder', 'Reavis' bears very small leaves and is very low growing, resembling creeping thyme. In addition, the flowers of 'Reavis' appear in early spring only, whereas 'Blue Yonder' blooms throughout spring and into early summer, and is exceptionally floriferous.

In comparison with 'Blue Yonder', 'Tidal Pool' bears smaller and more rounded leaves and bears fewer flowers. The leaves 'Blue Yonder' are elliptical and three times longer than the leaves of 'Tidal Pool'. In addition, the racemose inflorescence of 'Blue Yonder' is three times longer and bears many more flowers than an inflorescence of 'Tidal Pool'.

We claim:

1. A new and distinct variety of *Veronica* plant named 'Blue Yonder' as described and illustrated herein.

* * * * *